United States Patent
Dickens et al.

(10) Patent No.: US 10,188,144 B2
(45) Date of Patent: Jan. 29, 2019

(54) AEROSOL-FORMING MEMBER COMPRISING A SHEET OF MATERIAL HAVING A NON-PLANAR INNER MAJOR SURFACE

(71) Applicant: BATMark Limited, London (GB)

(72) Inventors: Colin John Dickens, London (GB); Rory Fraser, London (GB); Helmut Buchberger, St. Florian (AT)

(73) Assignee: Batmark Limited, London (GB)

( * ) Notice: Subject to any disclaimer, the term of this patent is extended or adjusted under 35 U.S.C. 154(b) by 9 days.

(21) Appl. No.: 15/115,559

(22) PCT Filed: Jan. 28, 2015

(86) PCT No.: PCT/GB2015/050191
§ 371 (c)(1),
(2) Date: Jul. 29, 2016

(87) PCT Pub. No.: WO2015/114325
PCT Pub. Date: Aug. 6, 2015

(65) Prior Publication Data
US 2017/0188629 A1    Jul. 6, 2017

(30) Foreign Application Priority Data

Jan. 29, 2014 (GB) .................................. 1401524.2

(51) Int. Cl.
*A24F 13/00* (2006.01)
*A24F 17/00* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC ...... A24F 47/008; A24F 47/00; A24F 47/004; A61M 11/04
See application file for complete search history.

(56) References Cited

U.S. PATENT DOCUMENTS

| 5,135,009 A | 8/1992 | Müller |
| 5,591,368 A | 1/1997 | Fleischhauer et al. |

(Continued)

FOREIGN PATENT DOCUMENTS

| AT | 511344 A4 * | 11/2012 | .......... A61M 11/041 |
| EP | 2 340 729 A1 | 7/2011 | |

(Continued)

OTHER PUBLICATIONS

International Search Report for corresponding International App No. PCT/GB2015/050191 dated Apr. 10, 2015; 4 pages.

(Continued)

*Primary Examiner* — Abdullah Riyami
*Assistant Examiner* — Thang Nguyen
(74) *Attorney, Agent, or Firm* — Patterson Thuente Pedersen, P.A.

(57) ABSTRACT

An aerosol-forming member comprising a sheet of material configured to wick and to heat a solution is disclosed. The sheet of material comprises a non-planar inner major surface having a capillary structure configured to emit vapor during use, and an outer major surface that is configured to emit less vapor than the inner major surface during use.

16 Claims, 13 Drawing Sheets

(51) Int. Cl.
  *A24F 25/00* (2006.01)
  *A24F 47/00* (2006.01)
  *A61M 15/06* (2006.01)
  *A61M 11/04* (2006.01)
  *A61M 16/00* (2006.01)

(52) U.S. Cl.
  CPC ............... *A61M 2016/0024* (2013.01); *A61M 2205/3653* (2013.01); *A61M 2205/8206* (2013.01)

(56) References Cited

U.S. PATENT DOCUMENTS

| | | | |
|---|---|---|---|
| 8,511,318 B2* | 8/2013 | Hon | A24F 47/002 131/273 |
| 2008/0092912 A1* | 4/2008 | Robinson | A24F 47/008 131/200 |
| 2009/0272379 A1* | 11/2009 | Thorens | A24F 47/008 128/202.21 |
| 2011/0155153 A1* | 6/2011 | Thorens | H05B 3/58 131/329 |
| 2011/0155718 A1 | 6/2011 | Greim et al. | |
| 2011/0226236 A1* | 9/2011 | Buchberger | A61M 11/041 128/200.23 |
| 2013/0081623 A1* | 4/2013 | Buchberger | A61M 11/041 128/203.27 |
| 2014/0353856 A1* | 12/2014 | Dubief | A24D 3/041 261/128 |
| 2016/0073693 A1 | 3/2016 | Reevell | |
| 2016/0106154 A1 | 4/2016 | Lord | |
| 2016/0106155 A1 | 4/2016 | Reevell | |
| 2016/0206003 A1* | 7/2016 | Yamada | A24F 47/008 |
| 2016/0353801 A1* | 12/2016 | Zinovik | A24F 47/008 |
| 2017/0027225 A1 | 2/2017 | Buchberger | |
| 2017/0188630 A1 | 7/2017 | Buchberger | |
| 2017/0197044 A1* | 7/2017 | Buchberger | A61M 11/042 |
| 2017/0197046 A1* | 7/2017 | Buchberger | A61M 11/041 |

FOREIGN PATENT DOCUMENTS

| | | |
|---|---|---|
| EP | 2 468 118 A1 | 6/2012 |
| JP | H 2-65524 | 3/1990 |
| JP | 1993/309136 | 5/1992 |
| JP | H05-309136 | 11/1993 |
| JP | 2012/506263 | 3/2012 |
| JP | A 2013516159 | 5/2013 |
| RU | 201201204 A | 7/2013 |
| RU | 132318 U1 | 9/2013 |
| WO | WO 94/06314 | 3/1994 |
| WO | WO 2013/057185 A1 | 4/2013 |
| WO | WO 2014/012894 | 1/2014 |
| WO | WO 2014/012894 A1 | 1/2014 |

OTHER PUBLICATIONS

Written Opinion of the International Searching Authority for corresponding International App No. PCT/GB2015/050191 dated Apr. 10, 2015; 8 pages.
International Preliminary Report on Patentability for corresponding International App No. PCT/GB2015/050191 dated Apr. 19, 2016; 19 pages.
Written Opinion of the International Preliminary Examining Authority for corresponding International App No. PCT/GB2015/050191 dated Jan. 20, 2016; 8 pages.
Japanese Office Action, Application No. 2016-548374, dated Apr. 29, 2017, 3 pages ( 6 pages with translation).
Russian Office Action, Application No. 2016131274, dated Nov. 14, 2017, 1 page.
Korean Office Action, Application No. 10-2016-7020981, dated Jul. 6, 2018, 2 pages.

* cited by examiner

AEROSOL-FORMING MEMBER COMPRISING A SHEET OF MATERIAL HAVING A NON-PLANAR INNER MAJOR SURFACE

RELATED APPLICATIONS

The present application is a National Phase entry of PCT Application No. PCT/GB2015/050191, filed on 28 Jan. 2015, which claims priority to GB Patent Application No. 1401524.2, filed on 29 Jan. 2014, which are hereby fully incorporated herein by reference.

TECHNICAL FIELD

The disclosure relates to an aerosol-forming member for an aerosol delivery device. The disclosure also relates to an aerosol delivery device component comprising the aerosol-forming member, and an aerosol delivery device comprising said aerosol delivery device component.

BACKGROUND

An aerosol delivery device is a device used for delivering substances into the body via the lungs. One type of aerosol delivery device forms a vapor of a solution in which the substances are dissolved. This vapor condenses within the aerosol delivery device as it mixes with air so as to form droplets or aerosol which is suitable for inhalation. These aerosol delivery devices may comprise a heating element that is configured to evaporate the solution held within the aerosol delivery device so as to form said aerosol. Alternatively, some aerosol delivery devices may utilize piezo atomizers to generate the aerosol.

SUMMARY

According to embodiments, there is provided an aerosol-forming member comprising a sheet of material configured to wick and to heat a solution, the sheet of material comprising a non-planar inner major surface having a capillary structure configured to emit vapor during use, and an outer major surface that is configured to emit less vapor than the inner major surface during use.

In one embodiment, the sheet of material is non-planar. The sheet of material may have a U-shaped, Ω-shaped or V-shaped cross-section. Alternatively, the sheet of material may have a partial polygonal cross-section.

In one embodiment, the capillary structure extends throughout the whole sheet of material, and the sheet of material is formed from a heatable material.

In one embodiment, the sheet of material comprises a single layer formed with the capillary structure, the sheet of material is made of a heatable material.

In another embodiment, the sheet of material comprises a first layer that is formed from a heatable material and a second layer comprising the capillary structure, wherein the first layer forms the outer major surface and the second layer forms the inner major surface.

In one embodiment, the inner and the outer major surfaces may be porous, and the pore size of the outer major surface is smaller than the pore size of the inner major surface such that the amount of vapor emitted from the outer major surface is less compared to the inner major surface when in use.

In one embodiment, the outer major surface is non-porous such that the amount of vapor emitted from the outer major surface is less compared to the inner major surface when in use.

In another embodiment, the aerosol-forming member further comprises a cover located against the outer major surface such that the amount of vapor emitted from said outer major surface is less compared to the inner major surface when in use.

In yet another embodiment, the outer major surface is vapor impermeable.

According to another aspect, there is provided an aerosol delivery device component comprising an air inlet and an air outlet fluidly communicating via an aerosol chamber defined by chamber walls, and an aerosol-forming member as described above which is at least partially located in the aerosol chamber. In another embodiment, the whole aerosol-forming member is located in the aerosol chamber.

In one embodiment, the aerosol-forming member is positioned within the aerosol chamber such that the outer and inner major surfaces are aligned with a direction of flow of air through the aerosol chamber.

In another embodiment, the chamber walls comprise a chamber side wall wherein at least a portion of the chamber side wall follows the contour of the outer major surface of the sheet of material.

The sheet of material may comprise two opposing ends that are attached to one of the chamber walls such that the sheet of material and said chamber wall are forming a passage disposed in the aerosol chamber.

In one embodiment, the chamber walls may at least partially comprise a heat shield.

According to yet another aspect, there is provided an aerosol delivery device comprising an aerosol delivery device component as described above or an aerosol-forming member as described above.

In a broad aspect of the present disclosure, there is disclosed an aerosol-forming member comprising a non-planar sheet of material configured to wick and to heat a solution, the sheet of material comprising an inner major surface having a capillary structure configured to emit vapor during use, and an outer major surface configured to emit vapor during use, wherein the sheet of material is configured to provide an aerosol adjacent to the inner major surface with an aerosol density that is greater than that of an aerosol provided adjacent the outer major surface.

BRIEF DESCRIPTION OF THE DRAWINGS

Embodiments will now be described, by way of example only, with reference to the accompanying drawings in which.

DETAILED DESCRIPTION

Figure 1:
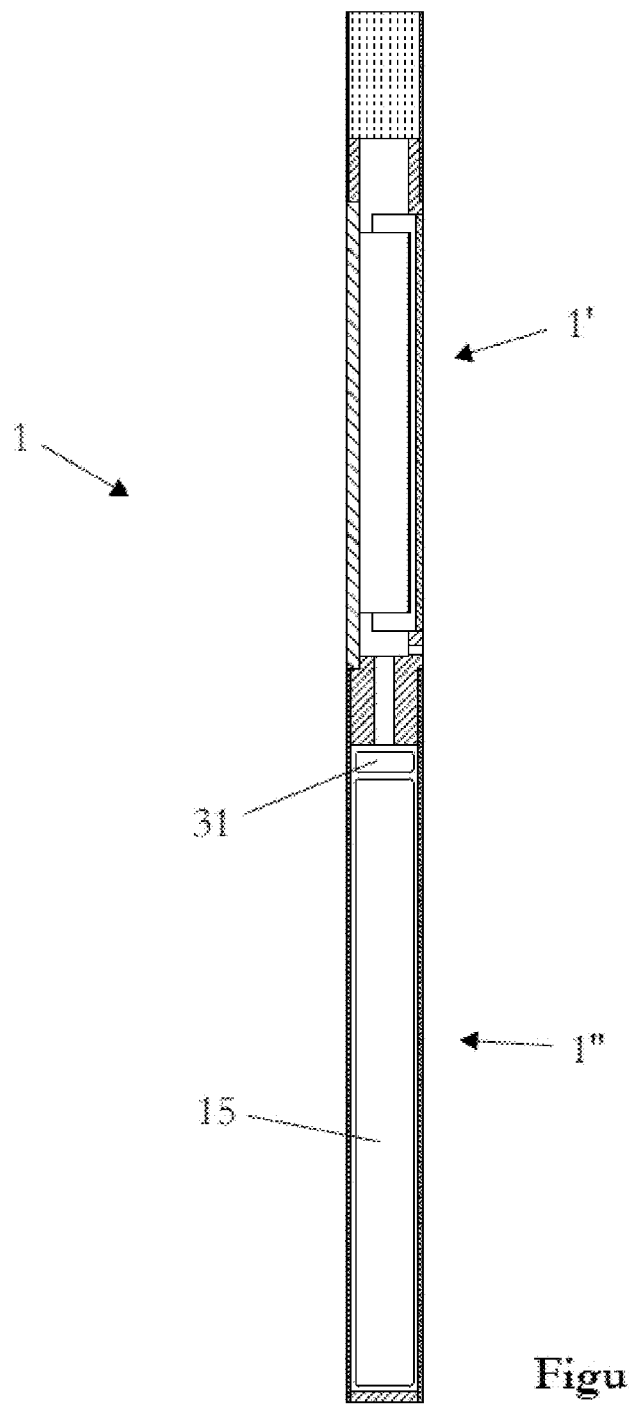
FIG. 1 shows a cross-sectional side view of an aerosol delivery device comprising an aerosol-forming member according to an embodiment.

Referring now to FIG. 1, an aerosol delivery device 1 according to an embodiment is disclosed. The aerosol delivery device comprises an aerosol delivery device component 1', and an energy store component 1". The aerosol delivery device component 1' is removably attachable to the energy store component 1", however it is envisaged that in an alternative embodiment, the aerosol delivery device component 1' and the energy store component 1" are inseparable such that they form as a single component.

The aerosol delivery device component 1' may be disposable and the energy store component 1" may be reusable. However, it is envisaged that when the two components are formed as a single component then the aerosol delivery device may be disposable or reusable.

The energy source component 1" comprises a housing holding a battery 15 and an electric circuitry 31 as shown in FIG. 1. It should be appreciated that an alternative power source to a battery may be used.

Figure 2:
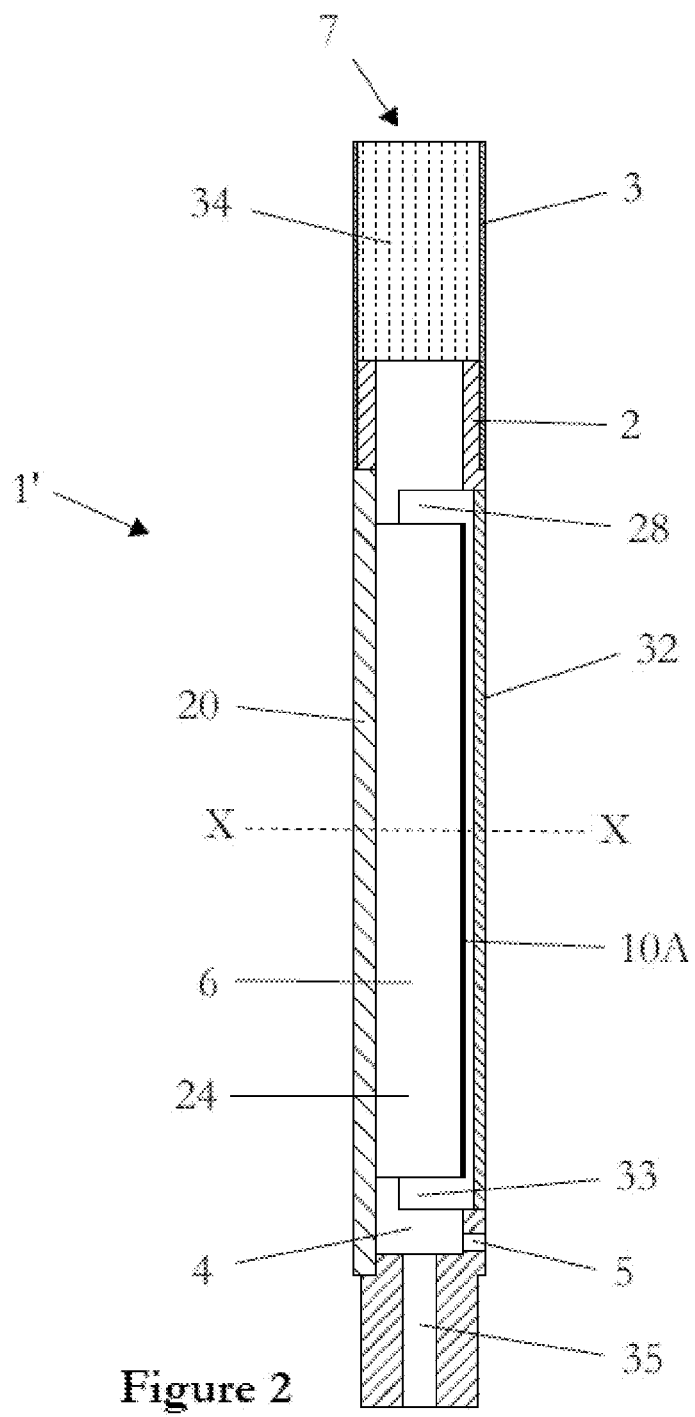
FIG. 2 shows a cross-sectional side view of an aerosol delivery device component comprising an aerosol-forming member according to an embodiment.

The aerosol delivery device component 1' is shown in greater detail in FIG. 2 and it comprises a housing 2 formed with a mouthpiece 3 at one end and an attachment end formed with a connecting passage 35 at the opposite end. The connecting passage 35 electrically connects components held in the aerosol delivery device component 1' with the battery 15 disposed in the energy store component 1" via the electric circuitry 31.

The housing 2 is further formed with an air passage extending through the aerosol delivery device component 1'. The air passage comprises an air inlet 5, plenum chamber 4, chamber inlet 33, aerosol chamber 6, chamber outlet 28 and outlet aperture 7. In use air is drawn in through the air inlet 5, into the plenum chamber 4, then to the chamber inlet 33 which supplies the air into the aerosol chamber 6, the air then exits the aerosol chamber 6 via chamber outlet 28 and leaves the aerosol delivery device component 1' via the outlet aperture 7 formed in the mouthpiece 3.

Figure 3:
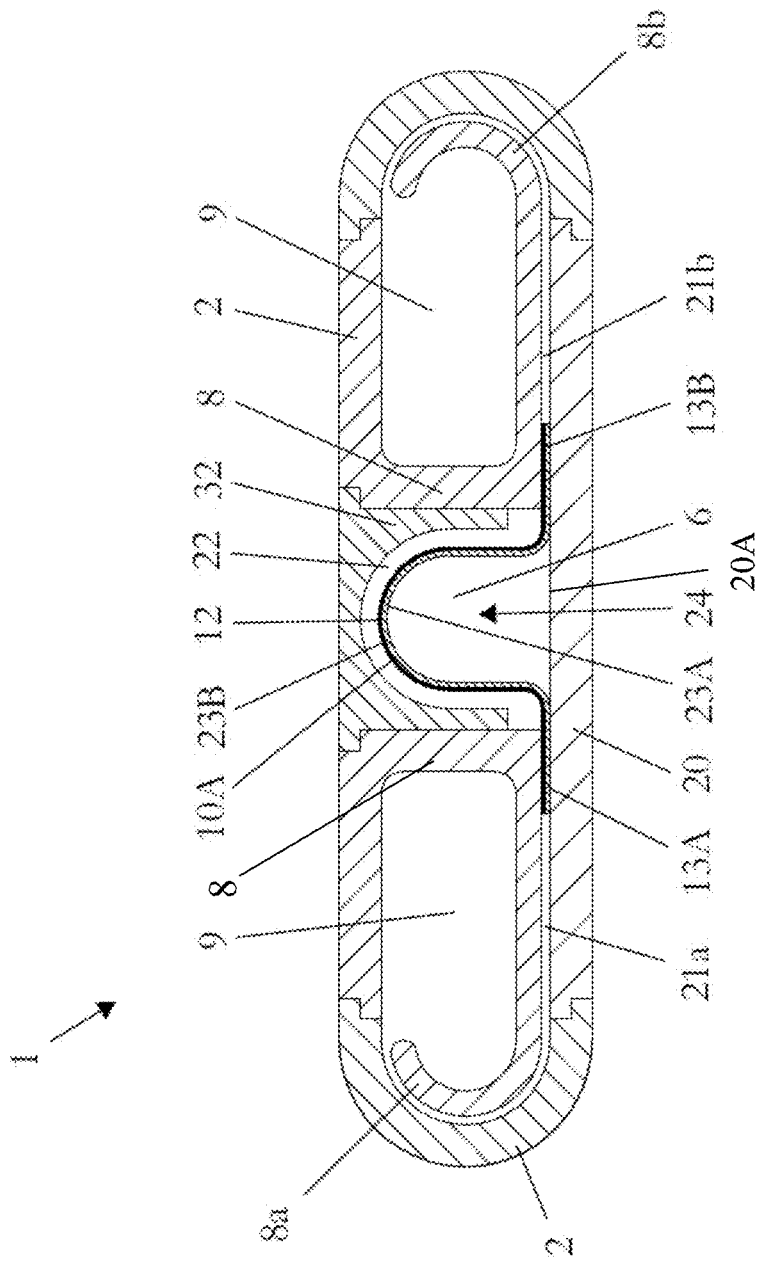
FIG. 3 shows a cross-sectional view of the aerosol delivery device along the line X-X of FIG. 2.

FIG. 3 illustrates a cross-sectional view of the aerosol delivery device component 1' along line X-X shown in FIG. 2. As can be seen in FIG. 3, the aerosol chamber 6 is located in the center of the housing and is defined by chamber walls. The chamber walls comprise two partitioning walls 8, a chamber side wall 32 and a support plate 20 as explained in more detail below. An aerosol-forming member 10A according to an embodiment is located in the aerosol chamber 6. On opposite sides of each partitioning walls 8 relative to the aerosol chamber 6, are two solution reservoirs 9 configured to contain a solution.

According to one embodiment, the aerosol-forming member 10A may comprise a sheet of material having a single layer that is configured to wick and heat a solution. Thus, the sheet of material can absorb solution from the solution reservoirs 9 and thereafter heat it up so that it evaporates and forms a vapor. The sheet of material is sheet-like in nature and has a rectangular shape. However, it should be understood that the sheet of material may be of any shape, for example, circular, oval or square. The sheet of material comprises inner and outer major surfaces 23A, 23B. The sheet of material may comprise an open-pored structure, foam structure, mesh structure or interconnecting network of pores, all of which form a capillary structure. The capillary structure enables the aerosol-forming member 10A to wick or absorb a solution. The term "capillary structure" used herein is to be understood as a structure through which liquid or a solution can travel as a result of capillary action.

In one embodiment of the aerosol-forming member 10A, the sheet of material may be made of a porous granular, fibrous or flocculent sintered metal(s) so as to form said capillary structure. In another embodiment, the sheet of material comprises an open-pored metallic foam or a group of layers of wire mesh or calendered wire mesh which also form a capillary structures. The sheet of material may be made of stainless steel. It is envisaged that a thin support layer (not shown) may be sintered onto one or both of the inner and outer major surfaces 23A, 23B. Such a support layer may be formed from a wire mesh made of stainless steel.

The capillary structure is exposed at least on the inner major surface 23A of the aerosol-forming member 10A. For example, the aerosol-forming member 10A may be formed with a capillary structure that extends throughout the whole aerosol-forming member 10A such that it is exposed on both inner and outer major surfaces 23A, 23B of the sheet of material. In another embodiment, the aerosol-forming member 10A is configured such that the capillary structure does not extend throughout the whole aerosol-forming member 10A. For example, the capillary structure may only be exposed on the inner major surface 23A or a section of the inner major surface 23A.

The outer major surface 23B of the sheet of material is configured to emit less vapor than the inner major surface 23A during use. This may be achieved by sealing the outer major surface 23B, for example, by locating a cover 12 against the outer major surface. The cover 12 may comprise of a thin layer made of a dielectric/non-conductive material. Alternatively, the outer major surface 23B itself may be modified appropriately, for example, by making it non-porous or by configuring it such that it has a smaller pore size than the inner major surface 23A.

The material from which the sheet of material is formed is heatable in that it comprises sufficient electrical resistivity so that when current is passed through, the sheet of material heats up to a temperature sufficient to cause the solution held in the capillary structure to evaporate or vaporize. In the embodiments as described above wherein the capillary structure extends throughout the whole sheet of material, the sheet of material can be considered to comprise a heating element formed with a capillary structure such that the heating element and the capillary structure are integrated and form a single entity or unit, and the sheet of material can be described as comprising a heating element and a wick that are arranged in the same surface.

In an alternative un-illustrated embodiment, the sheet of material may comprise a plurality of layers, for example it may comprise any combination of the aforementioned structures and materials, e.g. by providing multiple layers of different structures/materials, the layers being joined together, e.g. by sintering. One such alternative un-illustrated embodiment will now be described in more detail.

The aerosol-forming member comprises a sheet of material that is sheet-like in nature and formed from a plurality of layers. The sheet of material comprises a non-porous heatable first layer acting as a heating element and a second layer providing the capillary structure. The first layer is formed from a material that is configured to be heated up and may comprise a metal foil, it may be made of stainless steel or nickel chromium alloys. The second layer is formed with an open-pored structure, foam structure, mesh structure or interconnecting network of pores, all of which form a capillary structure. The capillary structure enables the aerosol-forming member 10A to wick or absorb a solution. This second layer may comprise a fiber web or fabric made of glass fibers, glass fiber yarns or any other non-conductive and inert, thus relatively non-heatable fiber materials. In this embodiment the sheet of material can be described as comprising a heating element and a wick that are arranged in parallel surfaces and are connected to each other. The second layer acts as a wick.

The first layer (heating element) and the second layer (wick having a capillary structure) are laid on top of each other so as to form a sheet of material having two opposing inner and outer major surfaces, wherein the capillary structure is exposed on the inner major surface. The layers may be connected to each other by mechanical or chemical means or by a heat treatment. In one embodiment, the layers are sintered to one another.

In an alternative embodiment both the first and the second layers may be made of a heatable material. For instance, the second layer may be made of a homogenous, granular, fibrous or flocculent sintered metal(s) or comprise an open-pored metallic foam or a wire mesh structure all of which form said capillary structure. In this embodiment the sheet of material can be described as comprising a heating element and a wick that are arranged in the same surface and in parallel surfaces.

In another embodiment, the first and second layers may be made of porous heatable material(s), such that both layers are configured to heat and wick a solution. In this embodiment the sheet of material can be described as comprising a heating element and a wick that are arranged in the same surface and in parallel surfaces.

In a further alternative un-illustrated embodiment, the sheet of material comprises a porous first layer having small sized pores and a second porous layer having larger sized pores than the first layer, thus both layers are formed with a capillary structure however the second layer forming the inner major surface can emit more vapor than the first layer forming the outer major surface. At least one of the two layers is formed from a heatable material as described above. Both layers may be formed with a structure and material as discussed above in relation to the capillary structure.

In yet an alternative un-illustrated embodiment, the sheet of material comprises a third layer that is similar to the second layer in that it comprises a capillary structure. The second and the third layers sandwich the first layer such that the capillary structure is exposed on both the inner and the outer major surfaces of the sheet of material.

The aerosol-forming member comprising a sheet of material formed from a plurality of layers as described according to any of the embodiments above may further comprise a cover closing or sealing the outer major surface so as to decrease the amount of vapor emitted from said outer major surface.

The sheet of material according to any of the above described embodiments has thickness or depth that falls within the range of 20-500 µm. Alternatively, the thickness falls within the range of 50 to 200 µm. The thickness or depth should be understood as meaning the distance between the inner and outer major surfaces 23A, 23B of the sheet of material.

Figure 4:
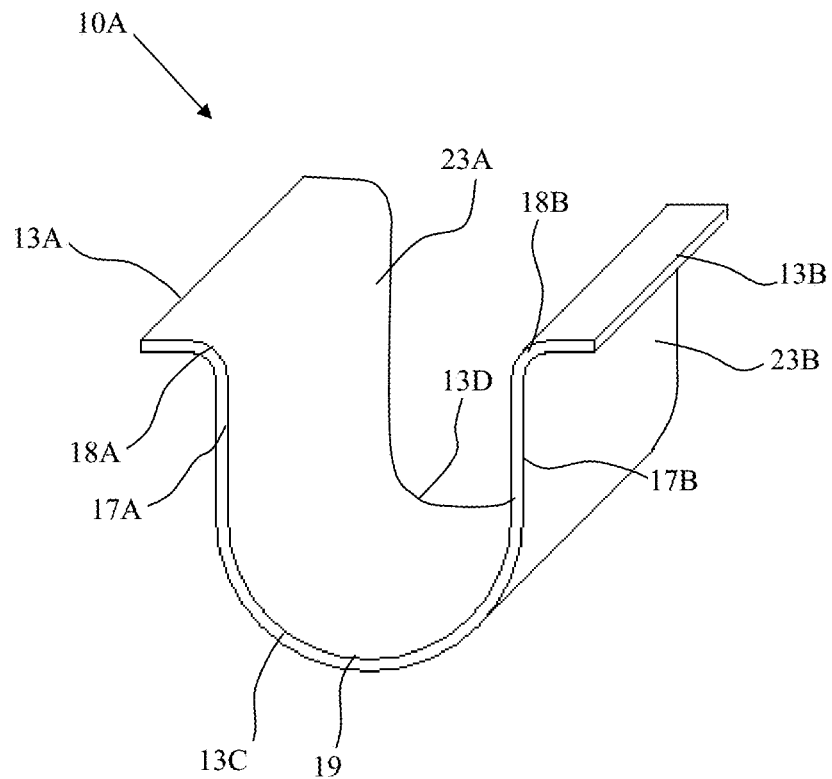
FIG. 4 shows a perspective view of the aerosol-forming member of FIG. 1.

Referring again to FIG. 3 as well as FIG. 4, the sheet of material is non-planar and has opposing short ends 13A, 13B and opposing longitudinal ends 13C, 13D. To manufacture the aerosol-forming element 10A the sheet of material is bent so that it has a curve-shape or a U-shape so as to form a channel 24, as described in more detail hereinafter. The short ends 13A, 13B of the aerosol-forming member 10A are flat and are integrally formed at approximately 90 degrees with respective parallel straight sections 17A, 17B of the aerosol-forming member via respective corner portions 18A, 18B. The ends of the straight sections 17A, 17B that are distal to the corner portions 18A, 18B are integrally formed with opposing ends of a semi-circular curved section 19 so that the aerosol-forming member 10A has an overall U-shaped cross-section, as can be seen in FIGS. 3 and 4. Thus, the aerosol-forming member 10A comprises sections that substantially face or oppose one another, i.e. they do not lie in the same plane. Advantageously, the curved or non-planar configuration increases the efficiency of the aerosol-forming member 10A, and the aerosol delivery device 1, can be made more compact. The efficiency of the aerosol-forming member 10A is defined as the ratio of aerosol particulate mass delivered to the user to vapor mass emitted from the aerosol-forming member 10A.

The flat short ends 13A, 13B of the aerosol-forming member 10A are mounted to the support plate 20 as shown in FIG. 3 so that a major surface 20A of the support plate 20 faces the inner curvature of the curved section 19. Thus, the aerosol-forming member 10A can be considered as bulging away from the support plate 20. As a result of this arrangement, the aerosol-forming member 10A is suspended in the aerosol chamber 6. It should be understood that the support plate 20 may be integral with the housing 2 or a discrete component. In an alternative embodiment, the support plate is omitted and the aerosol-forming member 10A is attached to the housing 2 such that the aerosol forming member 10A bulges away from the housing 2. In one embodiment the support plate 20 is a printed circuit board (PCB) and the aerosol-forming member 10A may be electrically connected to the PCB.

Moreover the aerosol-forming member 10A is disposed in the aerosol delivery device 1 such that the outer and inner major surfaces 23A, 23B are parallel or substantially aligned with a direction of flow of air through the aerosol chamber 6.

Furthermore, each short end 13A, 13B is securely located in gaps formed between the support plate 20 and the partitioning walls 8. The gaps have a width sufficient so as to provide a capillary effect, thus these gaps are referred to as first and second capillary gaps 21a, 21b. Each partitioning wall 8 comprises a tongue 8a, 8b that extend into respective solution reservoir 9 such that each capillary gap 21a, 21b is in fluid communication with the solution reservoirs 9. The three-dimensional geometry of the capillary gaps 21a, 21b help to surely feed solution from the solution reservoirs 9 to the flat short ends 13A, 13B of the aerosol-forming member 10A independent of the aerosol delivery device position.

The aerosol-forming member 10A is disposed in the aerosol chamber 6, with the chamber side wall 32 following or corresponding to the curvature of the aerosol-forming member 10A so that a heat insulating air gap 22 is formed therebetween. The chamber side wall 32 may be partially formed from a heat shield. The heat shield is formed from a heat resistant material like glass or ceramic and protects the housing 2 which is made of plastic from high temperatures. Alternatively, the housing 2 itself may be molded from a heat resistant plastic.

The inner major surface 23A of the aerosol-forming member 10A faces towards the major surface 20A of the support plate 20. Thus, the capillary structure is exposed or faces towards the major surface 20A of the support plate 20. Furthermore, the inner major surface 23A of the aerosol-forming member 10A form a channel 24 for directing or guiding the flow of aerosol formed from the evaporating vapor through the aerosol delivery device component 1'. This channel 24 is further enclosed so as to form a passage by the aerosol-forming member 10A being mounted on the support plate 20. The term "channel" used herein is to be understood as being formed from a non-planar surface or a plurality of surfaces that that lie in different planes.

The outer major surface 23B of the aerosol-forming member 10A faces towards the chamber side wall 32 and partitioning walls 8 and is configured to be vapor impermeable or vapor restrictive such that less amount of vapor is emitted from the outer major surface 23B compared to the inner major surface 23A. In the embodiment, where the aerosol-forming member 10A comprises a sheet of material having capillary structure exposed on both its inner and the outer major surface 23A, 23B, a cover 12 is positioned on the outer major surface 23B such that vapor is restricted from being emitted from the aerosol-forming member via the outer major surface 23B as explained above and illustrated in FIG. 3. Alternatively, the outer major surface 23B itself may be modified appropriately, e.g. by making the surface non-porous or by providing a pore size that is smaller than the pore size on the inner major surface 23A.

In alternative embodiments where the aerosol-forming member comprises a sheet of material comprising a non-porous heatable first layer, for instance a metal foil, and where the outer major surface is formed by said non-porous heatable layer, no cover is required as the heatable layer is non-porous and does not generally enable vapor to be emitted therethrough.

It should be understood that the above described embodiments prevent or reduce the amount of vapor emitted from the outer major surface of the aerosol-forming member 10A. Advantageously, these configurations reduce the amount of vapor and aerosol condensing on the chamber walls and/or partitioning walls 8. They also assist the emitted vapor to be directed towards the center of the channel 24 increasing vapor density and also guiding the aerosol formed from the vapor through the channel 24.

When the aerosol delivery device component 1' is attached to the energy store component 1" as shown in FIG. 1, the short ends 13A, 13B of the aerosol-forming member 10A are electrically connected via the electric circuitry 31 to the positive and negative terminals of the battery 15 respectively. When current is drawn from the battery 15 and through the sheet of material, the resistance of the sheet of material causes it to increase in temperature so that solution held in the pores or voids of the capillary structure evaporates. In the embodiment wherein the sheet of material comprises a non-porous heatable first layer, for instance a metal foil, and where the outer major surface is formed by said first layer, the resistance of said first layer causes the first layer, acting as a heating element, to increase in temperature. The first layer in turn heats up the adjacent second and/or third layers including the solution held in the pores or voids of the capillary structure of said second and/or third layers. In an alternative embodiment, the longitudinal ends 13C, 13D are connected to the terminals of the battery 15. In another embodiment, the current drawn from the battery 15, and the temperature level of the aerosol-forming member 10A may be controlled by a switching circuit, e.g. a Power-MOSFET switching circuit, included in the electrical circuitry 31.

Operation of the aerosol-forming member 10A will now be described with reference to FIGS. 1 to 4. In use, the user may manually activate the aerosol delivery device 1 or the aerosol delivery device may be activated automatically as the user starts puffing on the aerosol delivery device. This may be achieved by a pressure sensor connected to the electric circuitry 31 via the connecting passage 35. The pressure sensor may be located in the plenum chamber 4. When the aerosol delivery device is activated, the battery 15 provides a potential difference between the opposing short ends 13A, 13B or alternatively between the opposing longitudinal ends 13C, 13D of the aerosol-forming member 10A. This causes current to flow through the sheet of material such that the aerosol-forming member 10A increases in temperature. This increase in temperature causes the solution held in the capillary structure of the aerosol-forming member 10A to mainly evaporate from the inner major surface 23A so as to form a vapor. The evaporated solution or vapor mixes with air drawn by the user into the aerosol chamber 6, via air inlet 5, plenum chamber 4 and chamber inlet 33. The evaporated solution mixes with the air in the channel 24 formed by the inner major surface 23A of the aerosol-forming member 10A. As the vapor mixes with the air it condenses and forms droplets such that an inhalable aerosol is produced.

The cover 12 provided on the major outer surface 23B of the sheet of material as shown in FIG. 3 prevents or reduces the amount of solution evaporating from the major outer surface 23B of the sheet of material, thus minimizing unwanted condensation forming on the chamber walls. Similarly, in the alternative embodiments wherein the outer major surface 23B is not formed with a capillary structure, i.e. it is non-porous, solution is prevented or reduced from evaporating from said outer major surface 23B. Furthermore, by preventing or reducing the amount of solution from evaporating from the major outer surface 23B of the aerosol-forming member 10A and by the curvature of the inner major surface 23A directing the vapor towards the center of the channel 24, the vapor density in the channel 24 is increased, which means that more aerosol may be generated and inhaled by the user. Thus, the efficiency of the aerosol-forming member 10A is improved compared to planar aerosol-forming members known from the prior art.

After the aerosol-forming member 10A has been activated and aerosol has formed in the channel 24, the aerosol is drawn through the channel 24 as the user continues to inhale.

The curvature of the inner major surface 23A of the aerosol-forming member 10A guides or directs the aerosol through the aerosol chamber 6. The aerosol then exits the aerosol chamber 6 through a chamber outlet 28. The aerosol then passes through an optional aerosol refining member 34 provided in the housing 2, causing the aerosol to be cooled.

The refining member 34 may also contain flavoring agents like menthol that are released into the flow of aerosol, before entering the user's mouth via the outlet 7 provided in the mouthpiece 3. Meanwhile, the solution that has evaporated from the capillary structure of the aerosol-forming member 10A is replaced by fresh solution from the solution reservoirs 9 due to the capillary effect of the capillary gaps 21a, 21b and the capillary structure of the aerosol-forming member 10A as described above and fresh air enters the channel 24 via the air inlet 5, chamber plenum 4 and chamber inlet 33.

In one embodiment, a pressure drop element such as a flow resistor may be positioned in the plenum chamber 4 so that the flow of air into the aerosol chamber 6 can be controlled. The flow resistor may consist of a simple aperture or hole and may be identical to the air inlet 5 in the housing 2. Alternatively, the flow resistor may consist of a porous body similar to a cigarette filter providing the flow resistance of a conventional cigarette (not shown).

Conventional aerosol delivery devices may comprise a sponge to collect condensate that is not inhaled by the user so as to prevent condensation from accumulating on the internal walls and components. As embodiments minimize the amount of vapor condensing onto internal walls and components, a sponge is not required, which simplifies the manufacturing process and reduces costs. Furthermore, by minimizing or preventing the vapor from condensing onto the housing 2, the transfer of condensation heat to the housing 2 may be reduced, making the aerosol delivery device 1 more comfortable for the user to hold.

Figure 5:
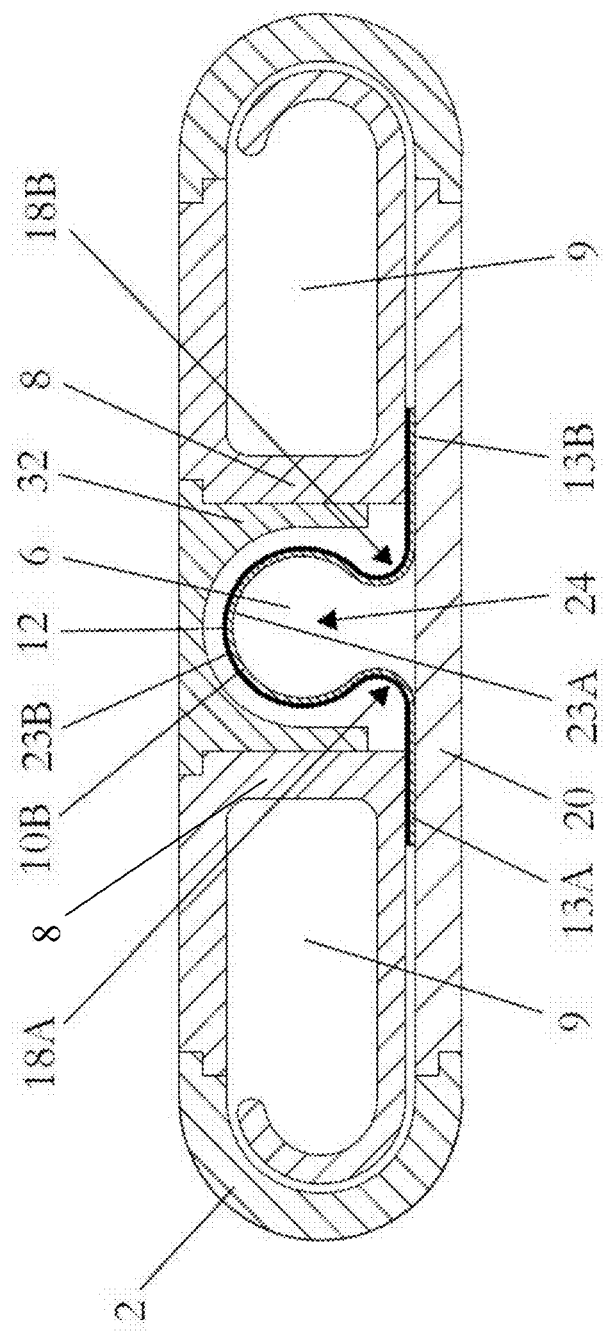
FIG. 5 shows a cross-sectional view of an aerosol delivery device comprising an aerosol-forming member according to another embodiment.

Referring now to FIG. 5, an aerosol-forming member 10B according to yet another embodiment is shown. The aerosol forming member 10B is similar to the embodiment described with reference to FIGS. 1 to 4, with like features retaining the same reference numerals. The straight sections 17A, 17B of the aerosol-forming member 10A are omitted and instead the corner portions 18A, 18B extend towards each other such that the cross-section of the aerosol-forming member has a partial circular, sack-like shape or Ω-shape (omega shape). In this embodiment, the aerosol-forming member 10B is curved or bent such that it forms an almost circular channel 24. Thus, the aerosol-forming member 10B comprises sections that substantially face or oppose one another, i.e. they do not lie in the same plane. Therefore, vapor is emitted towards a center of the channel 24 such that less vapor and/or aerosol gets in contact with the support plate 20. The vapor is almost completely enclosed by the inner major surface 23A. Thus, the efficiency of the aerosol-forming member 10B is improved compared to a planar aerosol-forming member. Moreover, it should be understood that this embodiment has the same advantages as those described with reference to FIG. 3. Furthermore, this embodiment may comprise any of the alternative configurations as described with reference to FIGS. 1 to 4.

Figure 6:
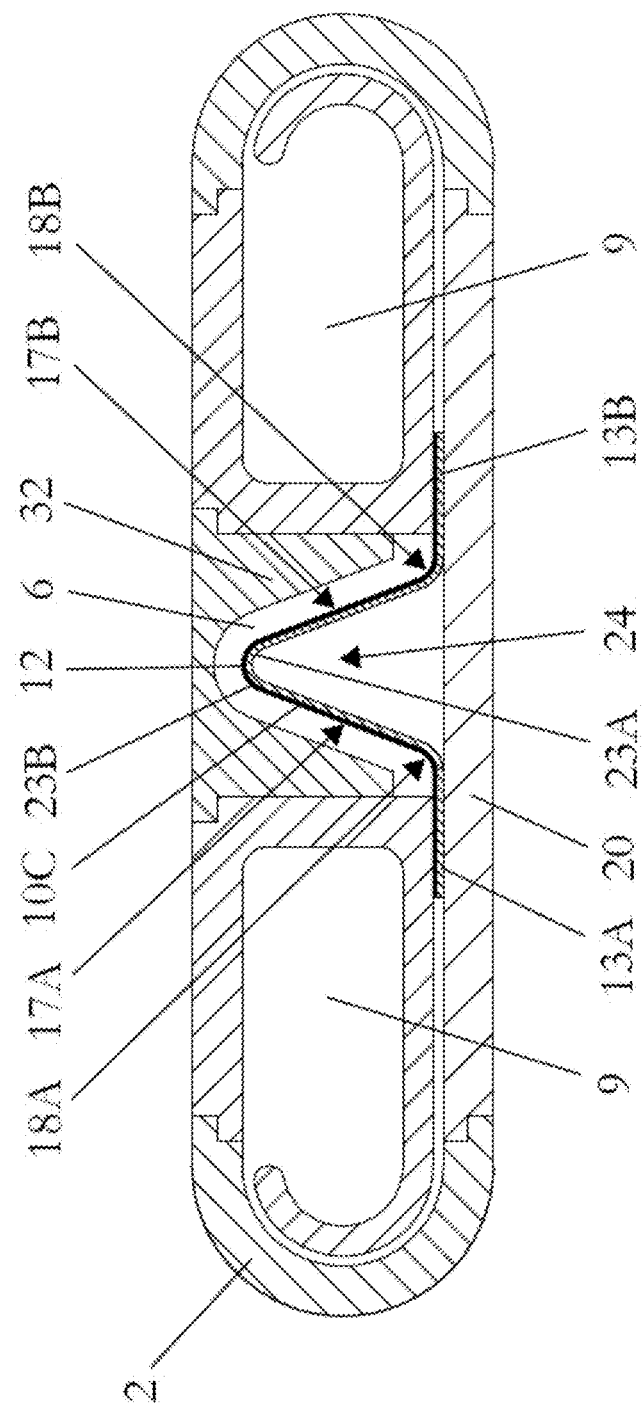
FIG. 6 shows a cross-sectional view of an aerosol delivery device comprising an aerosol-forming member according to yet another embodiment.

Referring now to FIG. 6, an aerosol-forming member 10C according to another embodiment is shown. The aerosol-forming member 10C is similar to the embodiment described with reference to FIGS. 1 to 4, with like features retaining the same reference numerals. However, the curved section 19 of the aerosol-forming member 10A is omitted and instead the straight sections 17A, 17B extend from the respective corner portions 18A, 18B at an oblique angle and meet each other such that the aerosol-forming member 10C has a V-shaped cross section. In one embodiment, the straight sections 17A, 17B may extend from the respective corner portions 18A, 18B at 45-80 degrees. A channel 24 is formed between the two straight sections 17A, 17B, in the 'trough' of the V-shape. Thus, the aerosol-forming member 10C comprises sections that substantially face or oppose one another, i.e. they do not lie in the same plane. As with the previously described embodiments, the surface area of the aerosol-forming member 10C is increased in comparison to a flat aerosol-forming member and therefore the aerosol delivery device can be made more compact. Moreover, it should be understood that this embodiment has the same advantages as those described with reference to FIGS. 1 to 4. Furthermore, this embodiment may comprise any of the alternative configurations as described with reference to FIGS. 1 and 4.

Figure 7:
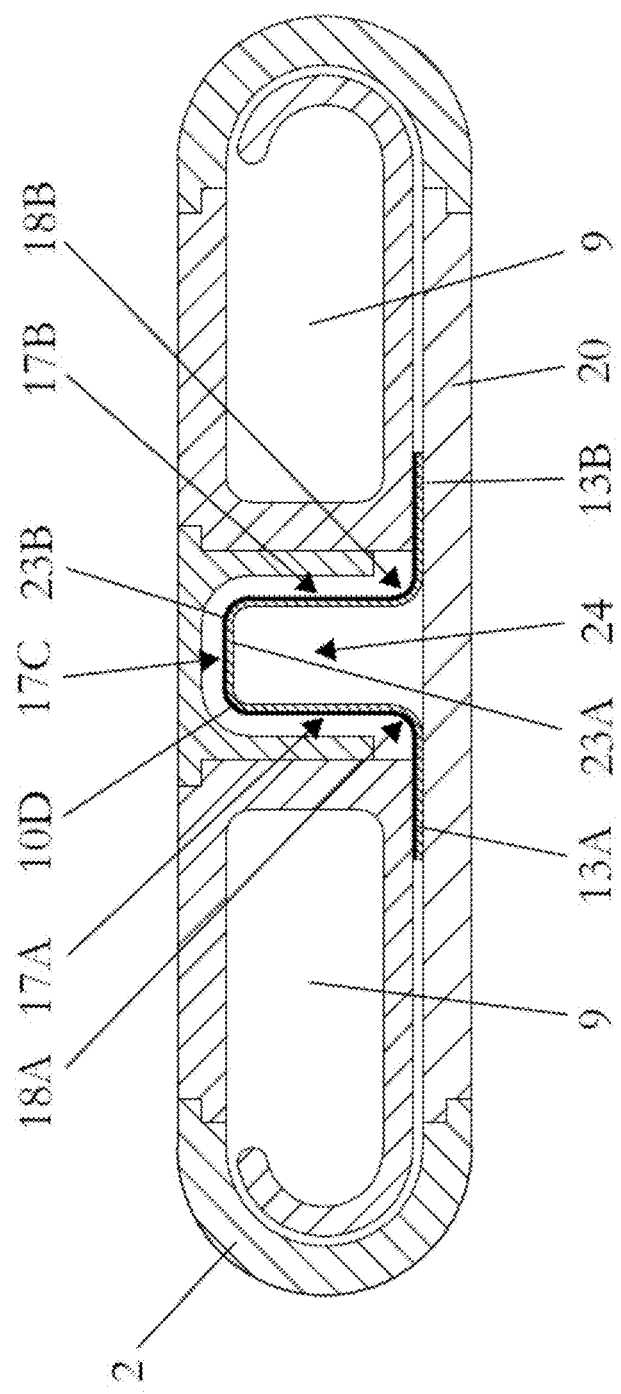
FIG. 7 shows a cross-sectional view of an aerosol delivery device comprising an aerosol-forming member according to a further embodiment.

Referring now to FIG. 7, an aerosol-forming member 10D according to a yet another embodiment is shown. The aerosol-forming member 10D is similar to the embodiment with reference to FIGS. 1 to 4, with like features retaining the same reference numerals. However, the curved section 19 of the aerosol-forming member 10A is omitted and instead the straight sections 17A, 17B are connected to a straight section 17C that extends at a right angle relative to the straight sections 17A, 17B so as to form a partial quadrilateral or tetragon. Alternatively a plurality of straight sections may be provided that extend at an angle relative to the straight sections 17A, 17B so as to form a partial polygon. All sections 17A, 17B, 17C are integrally formed. A channel 24 is formed in the space between the straight sections 17A, 17B, and the straight connecting section 17C. Thus, the aerosol-forming member 10D comprises sections that substantially face or oppose one another, i.e. they do not lie in the same plane. Moreover, it should be understood that this embodiment has the same advantages as those described with reference to FIGS. 1 to 4. Furthermore, this embodiment may comprise any of the alternative configurations as described with reference to FIGS. 1 and 4.

Although in the above described embodiments the short ends 13A, 13B, straight sections 17A, 17B or straight angled sections 17A, 17B (V-shape), corner portions 18A, 18B, curved section 19, straight connecting section 17C are integrally formed, in an alternative embodiment (not shown) they may be separate components that are bonded together.

It should be understood that the aerosol-forming member according to embodiments is not limited to being used with the aerosol delivery device described and shown herein. The aerosol-forming member according to embodiments can be used in any appropriate aerosol delivery device.

Figure 8:
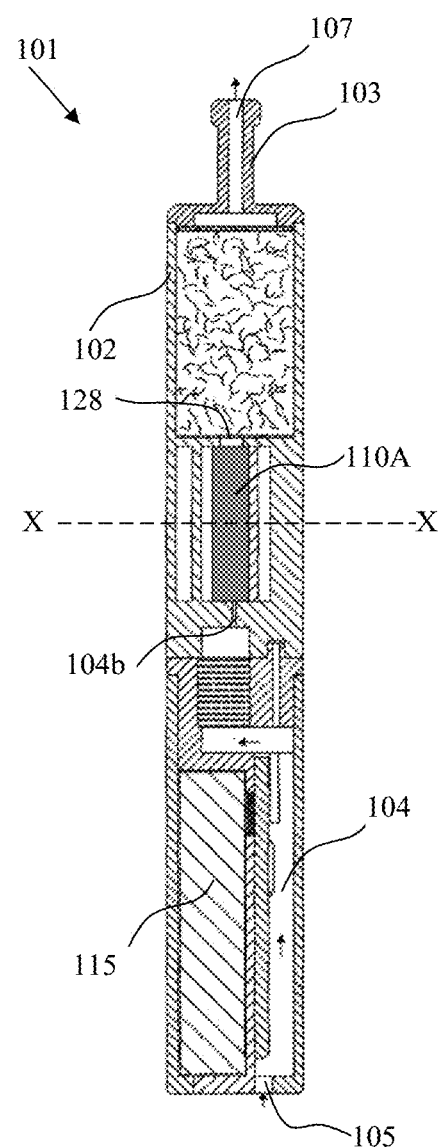
FIG. 8 shows a cross-sectional side view of an aerosol delivery device according to another embodiment.

For example, an alternative aerosol delivery device is shown in FIG. 8 and the aerosol-forming member according to embodiments can be implemented in such a device.

The aerosol delivery device 101 shown in FIG. 8, comprises a housing 102 formed with a mouthpiece 103. The housing 102 is further formed with an air passage extending through the aerosol delivery device 101. The air passage comprises an air inlet 105, an air channel 104a, a chamber inlet 104b, an aerosol chamber 106, a chamber outlet 128 and an outlet aperture 107.

Figure 9:
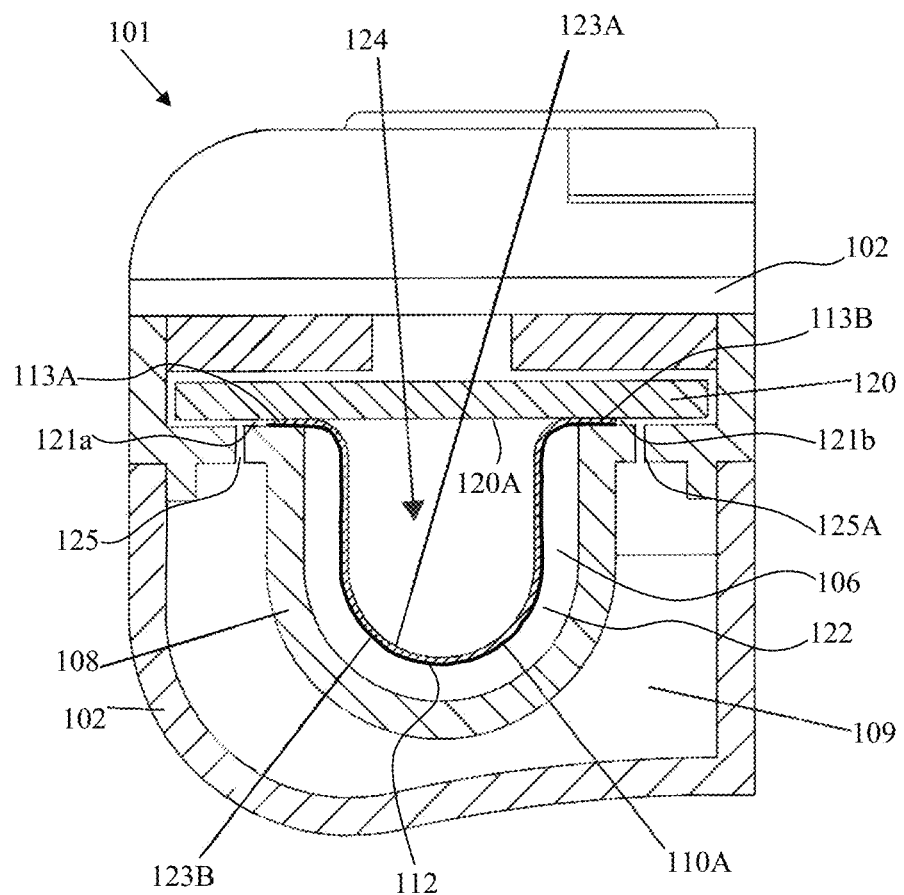
FIG. 9 shows a cross-sectional view of the aerosol delivery device along the line X-X of FIG. 8, the aerosol delivery device comprises an aerosol-forming member according to an embodiment.

A cross-section of the aerosol delivery device 101 shown in FIG. 8 along line X-X is shown in FIG. 9. The aerosol chamber 106 is defined by chamber walls which comprises a partitioning wall 108 and a support plate 120. On an opposite side of the partitioning wall 108 relative to the aerosol chamber is a solution reservoir 109.

An aerosol-forming member 110A is located in the aerosol chamber 106. The aerosol forming member 110A comprises a sheet of material having opposing inner and outer major surfaces 123A, 123B. The sheet of material may further comprise any combination of features described above with reference to FIGS. 1 to 7. The aerosol-forming member 110A may also comprise a cover 112 to prevent or reduce vapor from emitting from the outer major surface 123B.

The aerosol-forming member 110A is located in the aerosol chamber 106 in a similar manner as the embodiments described with reference to FIGS. 1 to 7, and so a detailed description will be omitted. However, it should be appreciated that the aerosol-forming member 110A comprises flat short ends 113A, 113B that are mounted to the support plate 120 as shown in FIG. 9 so that a major surface 120A of the support plate 120 faces a curved section of the inner major surface 123A. Thus, the aerosol-forming member 110A can be considered as bulging away from the support plate 120. As a result of this arrangement, the aerosol-forming member 110A is suspended in the aerosol chamber 106. In an alternative embodiment, the support plate 120 is omitted and the aerosol-forming member 110A is attached to the housing 102 such that the aerosol forming member 110A bulges away from the housing 102.

Furthermore, the inner major surface 123A of the aerosol-forming member 110A forms a channel 124 for directing or guiding the flow of aerosol formed from the evaporating vapor through the aerosol delivery device component 1'. This channel 124 is further enclosed so as to form a passage by the aerosol-forming member 110A being mounted on the support plate 120.

The aerosol-forming member 110A is disposed in the aerosol chamber 106, with partitioning wall 108 following or corresponding to the curvature of the aerosol-forming member 110A so that a heat insulating air gap 122 is formed therebetween. The partitioning wall 108 may be partially formed from a heat shield as described above. Alternatively, the housing 2 itself may be molded from a heat resistant plastic.

Furthermore, each short end 113A, 113B is securely located in gaps formed between the support plate 20 and the partitioning wall 8. The gaps have a width sufficient so as to provide a capillary effect, thus these gaps are referred to as first and second capillary gaps 121a, 121b.

Two supply apertures 125, 125A are formed in the partitioning wall 108 such that the solution reservoir 109 is in fluid communication with the first and second capillary gap 121a, 121b. The two supply apertures 125, 125A may be of such a width so as to provide a capillary effect assisting solution towards the first and second capillary gaps 121a, 121b. It should be understood that the aerosol delivery device 101 may comprise a single supply aperture or it may comprise more than two supply apertures to control the flow of solution to the capillary gaps 121a, 121b.

Figure 10:
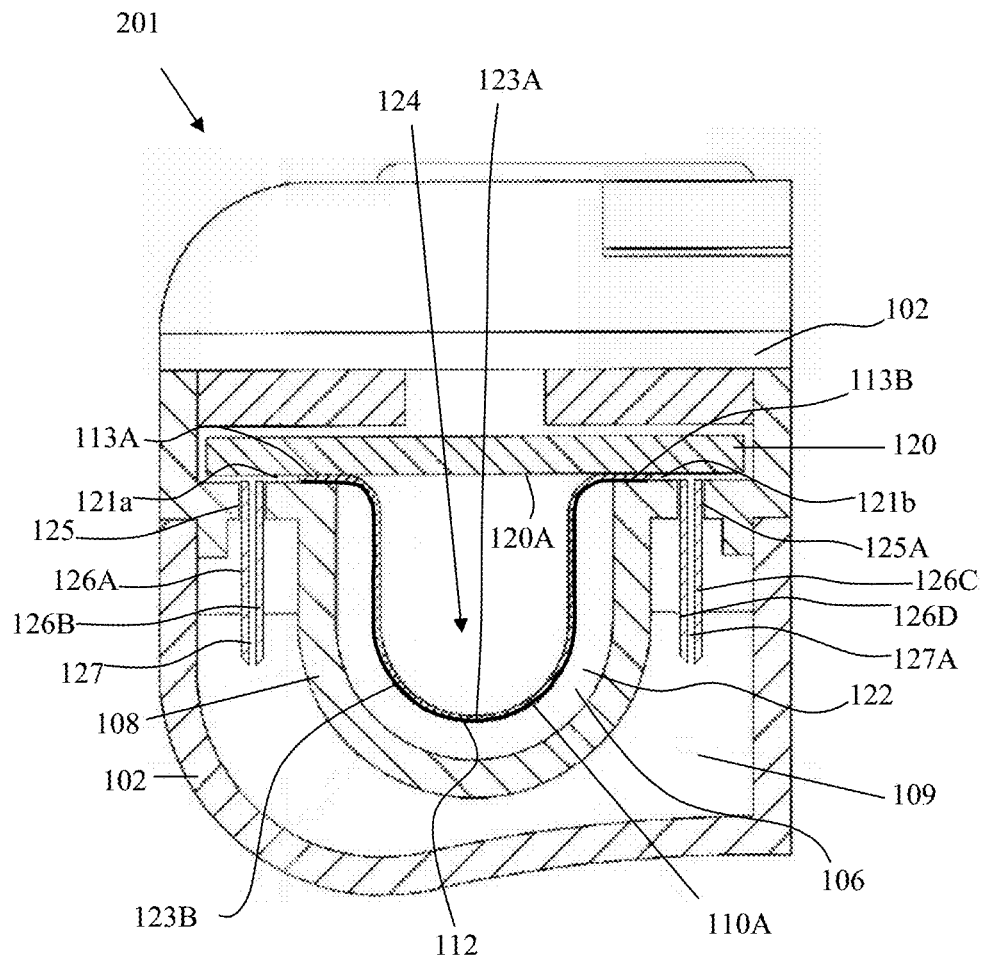
FIG. 10 shows a cross-sectional view of an aerosol delivery device according to another embodiment.

Referring now to FIG. 10, an alternative embodiment of an aerosol delivery device 201 is shown, with like features retaining the same reference numerals. In this embodiment, two parallel capillary plates 126A, 126B, 126C, 126D are located in each supply aperture 125, 125A. These extend out of each supply aperture 125, 125A and into the solution reservoir 109. Each pair of parallel capillary plates 126A, 126B, 126C, 126D are spaced from one another so as to form a capillary path 127, 127A. This arrangement causes each capillary path 127, 127A to be in fluid communication with the capillary structure of the aerosol-forming member 110A via the first and second capillary gap 121a, 121b respectively. The capillary plates 126A, 126B, 126C, 126D act as an extension of the capillary gaps 121a, 121b and can assist in supplying the aerosol-forming member 110A with solution. Therefore, in use, a solution held in the solution reservoir 109 moves by capillary action into each capillary path 127, 127A and is supplied, via the first and second capillary gaps 121a, 121b to the capillary structure at the short ends 113A, 113B of the aerosol-forming member 110A. The capillary structure provides a capillary effect similar to a wick, thus the capillary structure enables the aerosol-forming member 110A to absorb or suck up the solution provided to the first and second capillary gaps 121a, 121b such that the solution is distributed throughout the whole capillary structure of the aerosol-forming member 110A. It should be understood that only one or some of the supply apertures 125, 125A may be provided with capillary plates. It is also envisaged that the capillary plates may be substituted for a tube.

Figure 11:
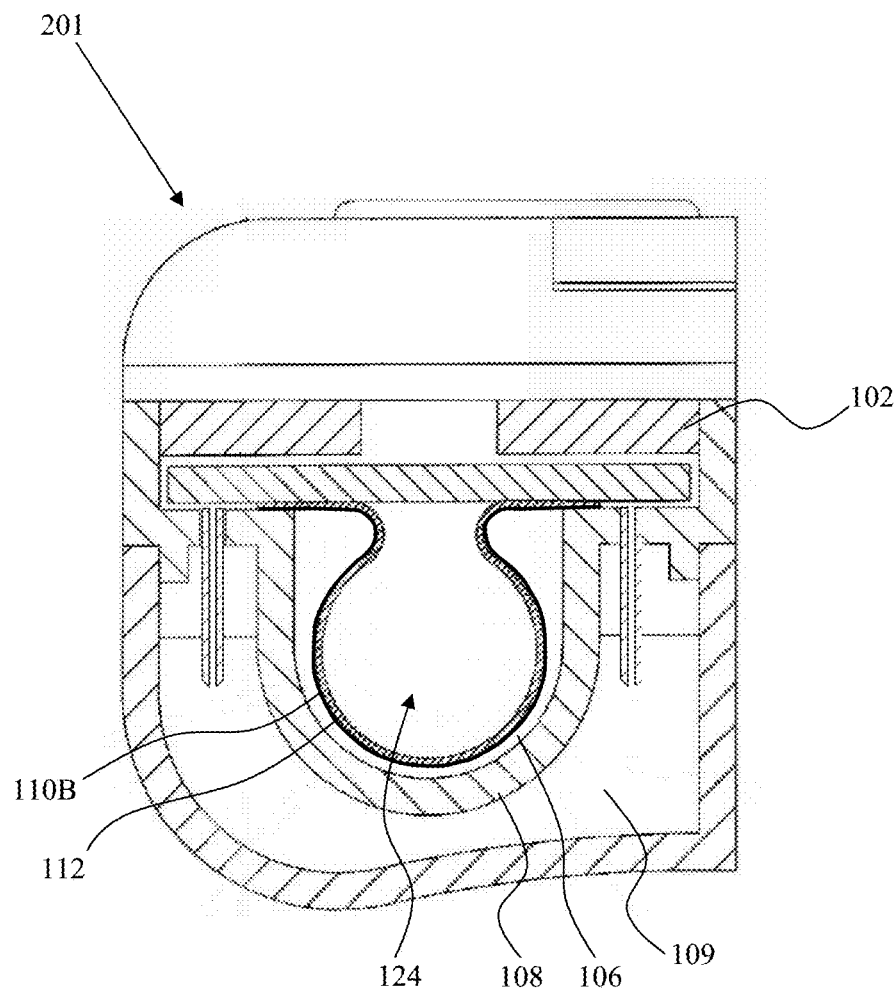
FIG. 11 shows a cross-sectional view of an aerosol delivery device according to yet another embodiment.

Referring now to FIG. 11, an aerosol-forming member 110B similar to that described with reference to FIG. 5 is located in the aerosol delivery device 201 described with reference to FIG. 10 with like features retaining the same reference numerals. The cross-section of the aerosol-forming member 110B has a partial circular, sack-like shape or Ω-shaped (omega shaped). In this embodiment, the aerosol-forming member 110B is curved or bent such that it forms a channel 124. Thus, the aerosol-forming member 110B comprises sections that substantially face or oppose one another, i.e. they do not lie in the same plane. Therefore, vapor is emitted towards a center of the channel 124 such that less vapor and/or aerosol gets in contact with the support plate 120. Furthermore, such a 'sack' or omega shaped cross-section increases the surface area of the aerosol-forming member 10B within the aerosol chamber 6, increasing the efficiency of the aerosol-forming member 10B, and thus the aerosol delivery device 201 can be made more compact. Moreover, it should be understood that this embodiment has the same advantages as those described with reference to the other figures. Furthermore, this embodiment may comprise any of the alternative configurations as described with reference to the other figures. For example, the aerosol-forming member 110B is shown in FIG. 11 to comprise an optional cover 112.

Figure 12:
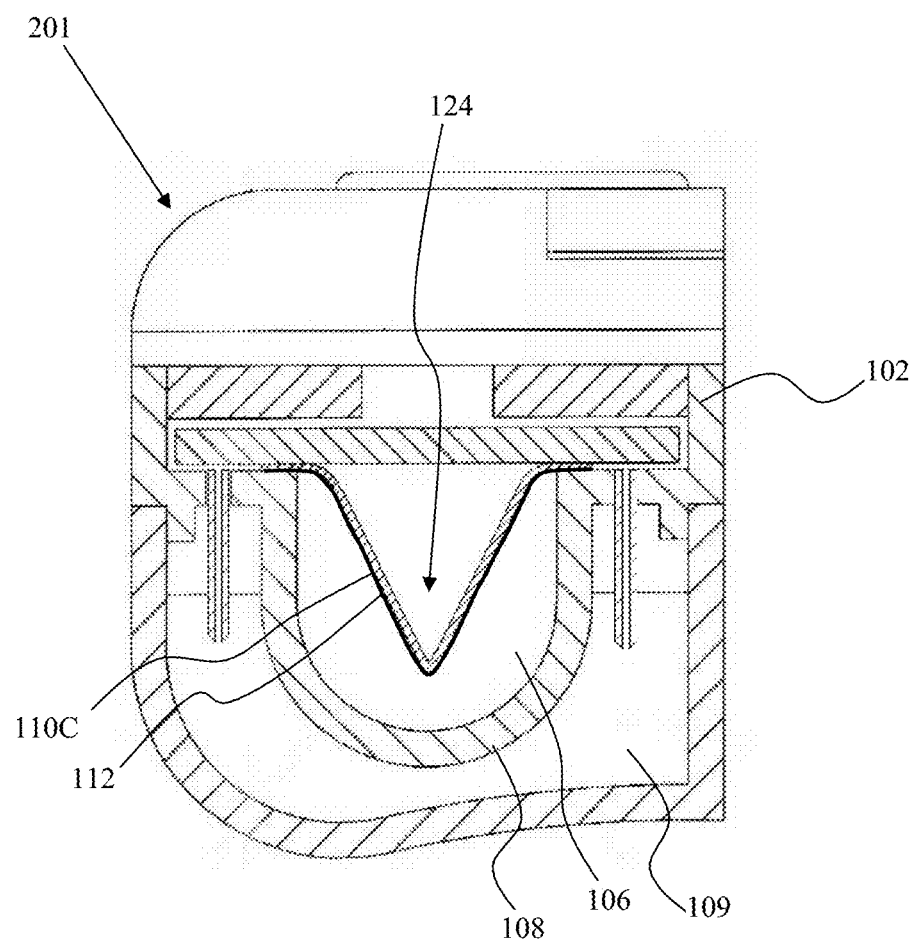
FIG. 12 shows a cross-sectional view of an aerosol delivery device according to a further embodiment.

Referring now to FIG. 12, an aerosol-forming member 110C similar to that described with reference to FIG. 6 is located in the aerosol delivery device 201 described with reference to FIG. 9 with like features retaining the same reference numerals. The cross-section of the aerosol-forming member 110C has a V-shaped cross section. The aerosol-forming member 110C comprises sections that substantially face or oppose one another, i.e. they do not lie in the same plane. A channel 124 is formed in the 'trough' of the V-shape. As with the previously described embodiments, the surface area of the aerosol-forming member 10C is increased in comparison to a flat aerosol-forming member and therefore the inhaler can be made more compact. Moreover, it should be understood that this embodiment has the same advantages as those described with reference to the other figures. Furthermore, this embodiment may comprise any of the alternative configurations as described with reference to the other figures. For example, the aerosol-forming member 110C is shown in FIG. 12 to comprise an optional cover 112.

Figure 13:
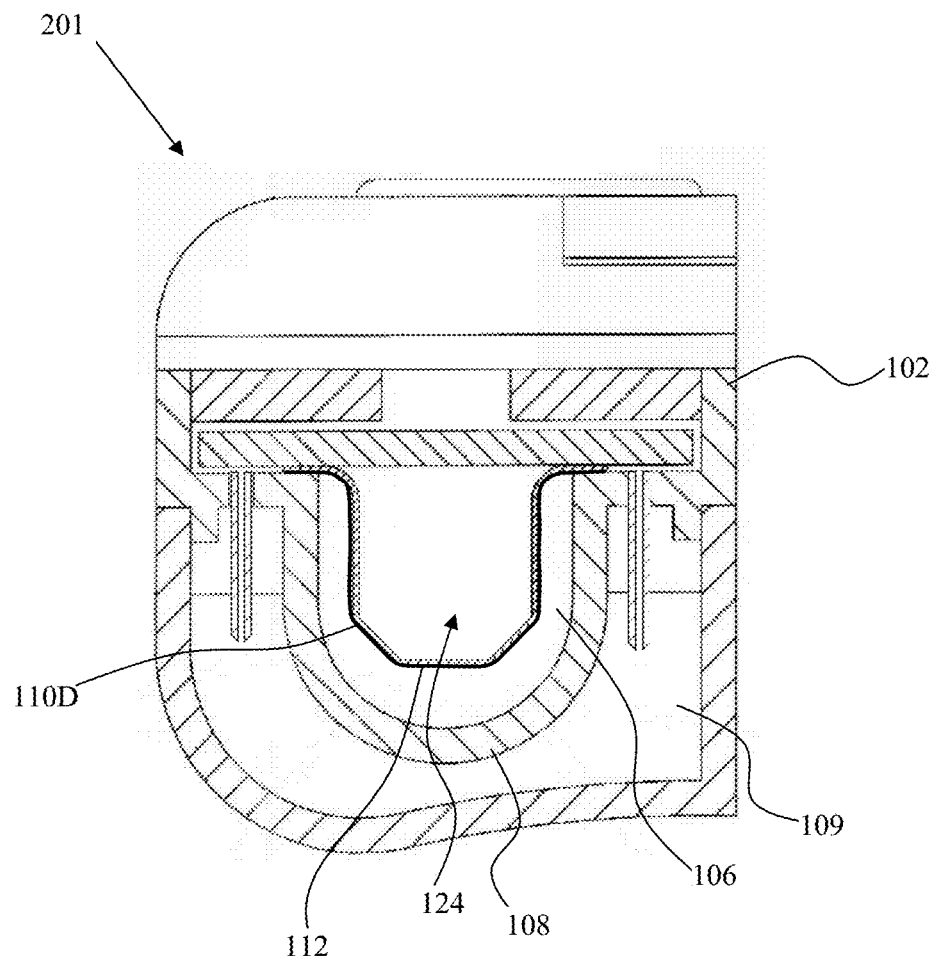
FIG. 13 shows a cross-sectional view of an aerosol delivery device according to another embodiment.

Referring now to FIG. 13, an aerosol-forming member 110D according to a yet another embodiment is shown. The aerosol delivery device is similar to the embodiment described with reference to FIG. 10, with like features retaining the same reference numerals. The aerosol-forming member 110D has cross-section that forms a partial polygon having a channel 124. Thus, the aerosol-forming member 110D comprises sections that substantially face or oppose one another, i.e. they do not lie in the same plane. Moreover, it should be understood that this embodiment has the same advantages as those described with reference to the other figures. Furthermore, this embodiment may comprise any of the alternative configurations as described with reference to the other figures. For example, the aerosol-forming member 110D is shown in FIG. 13 to comprise an optional cover 112.

Although the aerosol-forming members 110B, 110C, 110D described with reference to FIGS. 11 to 13 are shown to be positioned in aerosol delivery devices 201 comprising capillary plates extending into the solution reservoir 109, it should be understood that these capillary plates are optional. Furthermore, it should be understood that the aerosol-forming members 110A, 110B, 110C, 110D described with reference to FIGS. 9 to 13 can be located in any suitable aerosol delivery device.

The above described embodiments of the aerosol-forming member of the aerosol delivery device 1 are described for use with a solution. It should be understood that this solution may comprise certain constituents or substances that may have a stimulatory or therapeutic effect on the user. These constituents or substances may be of any kind that is suitable for being delivered via inhalation. The solution in which the constituents or substances are held or dissolved may primarily consist of water, ethanol, glycerol, propylene glycol or mixtures of the aforementioned solvents. By means of a sufficiently high degree of dilution in an easily volatile solvent, such as ethanol and/or water, even substances which are otherwise difficult to evaporate can evaporate in a substantially residue-free manner, and thermal decomposition of the liquid material can be avoided or significantly reduced.

It should be recognized that other shapes of aerosol forming-member are also intended to fall within the scope of the disclosure, provided that the cross-section of the aerosol-forming member follows a non-planar path and sections of the aerosol-forming member substantially face one another so as to form a channel that can guide or direct the flow of vapor and/or aerosol. The term "substantially" face or oppose one another is to be understood as sections that are parallel or at an angle to each other, and that do not lie in the same plane.

It should be appreciated that according to a broad aspect of the disclosure, the aerosol-forming member provided comprises a non-planar sheet of material configured to wick and to heat a solution. The sheet of material comprises an inner major surface having a capillary structure configured to emit vapor during use, and an outer major surface configured to emit vapor during use. The sheet of material is configured to provide an aerosol adjacent to the inner major surface with an aerosol density that is greater than that of an aerosol provided adjacent the outer major surface. The aerosol density should be understood to as aerosol particles in weight per volume of gas.

In order to address various issues and advance the art, the entirety of this disclosure shows by way of illustration various embodiments in which that which is claimed may be practiced and provide for superior aerosol-forming member, aerosol delivery device component and an aerosol delivery device. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. An aerosol-forming member comprising:
    a sheet of material configured to wick and to heat a solution, the sheet of material comprising a non-planar inner major surface having a capillary structure configured to emit vapor during use, and an outer major surface that is configured to emit less vapor than the inner major surface during use, wherein the inner major surface of the aerosol-forming member forms a channel.

2. An aerosol-forming member according to claim 1, wherein the sheet of material is non-planar.

3. An aerosol-forming member according to claim 1, wherein the sheet of material has a U-shaped, a-shaped, V-shaped or partial polygonal cross-section.

4. An aerosol-forming member according to claim 1, wherein the capillary structure extends throughout the whole sheet of material, and the sheet of material is formed from a heatable material.

5. An aerosol-forming member according to claim 1, wherein the sheet of material comprises a first layer that is formed from a heatable material and a second layer comprising the capillary structure, and the first layer forms the outer major surface and the second layer forms the inner major surface.

6. An aerosol-forming member according to claim 1, wherein the inner and outer major surfaces are porous, and a pore size of the outer major surface is smaller than a pore size of the inner major surface major such that an amount of vapor emitted from the outer major surface is less compared to the inner major surface when in use.

7. An aerosol-forming member according to claim 1, wherein the outer major surface is non-porous such that an amount of vapor emitted from the outer major surface is less compared to the inner major surface when in use.

8. An aerosol-forming member according to claim 1, further comprising a cover located against the outer major surface such that an amount of vapor emitted from said outer major surface is less compared to the inner major surface when in use.

9. An aerosol-forming member according to claim 1, wherein the outer major surface is vapor impermeable.

10. An aerosol delivery device component comprising:
    an air inlet and an air outlet fluidly communicating via an aerosol chamber defined by chamber walls; and
    an aerosol-forming member according to claim 1 which is at least partially located in the aerosol chamber.

11. An aerosol delivery device component according to claim 10, wherein the aerosol-forming member is positioned within the aerosol chamber such that the outer and inner major surfaces are aligned with a direction of flow of air through the aerosol chamber.

12. An aerosol delivery device component according to claim 10, wherein the chamber walls comprise a chamber side wall, and at least a portion of the chamber side wall follows the contour of the outer major surface of the sheet of material.

13. An aerosol delivery device component according to claim 10, wherein the sheet of material comprises two opposing ends that are attached to one of the chamber walls such that the sheet of material and said chamber wall form a passage disposed in the aerosol chamber.

14. An aerosol delivery device component according to claim 10, wherein the chamber walls at least partially comprise a heat shield.

15. An aerosol delivery device comprising an aerosol delivery device component as claimed in claim 10.

16. An aerosol delivery device comprising an aerosol-forming member as claimed in claim 1.

* * * * *

UNITED STATES PATENT AND TRADEMARK OFFICE
CERTIFICATE OF CORRECTION

PATENT NO. : 10,188,144 B2
APPLICATION NO. : 15/115559
DATED : January 29, 2019
INVENTOR(S) : Dickens Page 1 of 1

It is certified that error appears in the above-identified patent and that said Letters Patent is hereby corrected as shown below:

In the Claims

Column 14, Line 21, Claim 3:
Delete "a-shaped", insert --$\Omega$-shaped--

Signed and Sealed this
Ninth Day of July, 2019

Andrei Iancu
*Director of the United States Patent and Trademark Office*